(12) United States Patent
Hameed et al.

(10) Patent No.: US 7,752,050 B1
(45) Date of Patent: Jul. 6, 2010

(54) MULTIPLE-USER VOICE-BASED CONTROL OF DEVICES IN AN ENDOSCOPIC IMAGING SYSTEM

(75) Inventors: Salmaan Hameed, San Jose, CA (US); Amit A. Mahadik, San Jose, CA (US); Kiran A. Javadekar, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 938 days.

(21) Appl. No.: 10/934,019

(22) Filed: Sep. 3, 2004

(51) Int. Cl.
*G10L 21/00* (2006.01)
*G10L 21/06* (2006.01)
*A61B 1/00* (2006.01)

(52) U.S. Cl. .................. 704/275; 704/233; 704/270; 600/118

(58) Field of Classification Search .......... 704/233, 704/270, 275; 600/101, 118
See application file for complete search history.

(56) References Cited

U.S. PATENT DOCUMENTS

| | | | | |
|---|---|---|---|---|
| 4,184,048 A * | 1/1980 | Alcaide | .................. | 379/388.02 |
| 4,482,998 A * | 11/1984 | Marouf et al. | ......... | 379/202.01 |
| 4,499,578 A * | 2/1985 | Marouf et al. | ............. | 370/267 |
| 4,672,669 A * | 6/1987 | DesBlache et al. | .......... | 704/237 |
| 5,878,394 A * | 3/1999 | Muhling | ..................... | 704/275 |
| 6,192,339 B1 * | 2/2001 | Cox | ............................ | 704/270 |
| 6,453,020 B1 * | 9/2002 | Hughes et al. | ........... | 379/88.04 |
| 6,463,361 B1 * | 10/2002 | Wang et al. | .......... | 704/E15.045 |
| 6,496,107 B1 * | 12/2002 | Himmelstein | ............. | 340/426.1 |
| 6,791,601 B1 * | 9/2004 | Chang et al. | .................. | 348/65 |
| 6,842,510 B2 * | 1/2005 | Sakamoto | .................... | 704/275 |
| 7,127,392 B1 * | 10/2006 | Smith | .......................... | 704/233 |
| 7,158,860 B2 * | 1/2007 | Wang et al. | ................. | 700/245 |
| 7,236,929 B2 * | 6/2007 | Hodges | ...................... | 704/233 |
| 2002/0072912 A1 * | 6/2002 | Yen et al. | ..................... | 704/270 |
| 2003/0093503 A1 * | 5/2003 | Yamaki et al. | .............. | 709/220 |

OTHER PUBLICATIONS

Buess et al, "A new remote-controlled endoscope positioning system for endoscopic solo surgery". The FIPS Endoarm, Surg. Endosc. 14 (4), Apr. 2000, pp. 395-399.*
G.F. Buess et al., "A New Remote-Controlled Endoscope Positioning System for Endoscopic Solo Surgery", The FIPS Endoarm, Surgical Endoscopy Ultrasound and Intervention Techniques, Springer-Verlag New York Inc., Jul. 9, 1999, pp. 395-399.

* cited by examiner

*Primary Examiner*—James S Wozniak
(74) *Attorney, Agent, or Firm*—Blakely, Sokoloff, Taylor & Zafman LLP

(57) ABSTRACT

A multi-user voice control system for use in endoscopic imaging system includes a first input channel, a second input channel, an automatic speech recognizer (ASR), a control unit, and a selector. The first input channel receives speech of a first user, and the second input channel receives speech of a second user. The ASR recognizes speech received on the first channel and recognizes speech received on the second channel. The control unit enables the voice control system to control a device in the endoscopic imaging system in response to recognized speech. The selector selectively determines whether recognized speech associated with the first channel or recognized speech associated with the second channel is used to control the device, by applying a selection priority to the first and second channels.

34 Claims, 7 Drawing Sheets

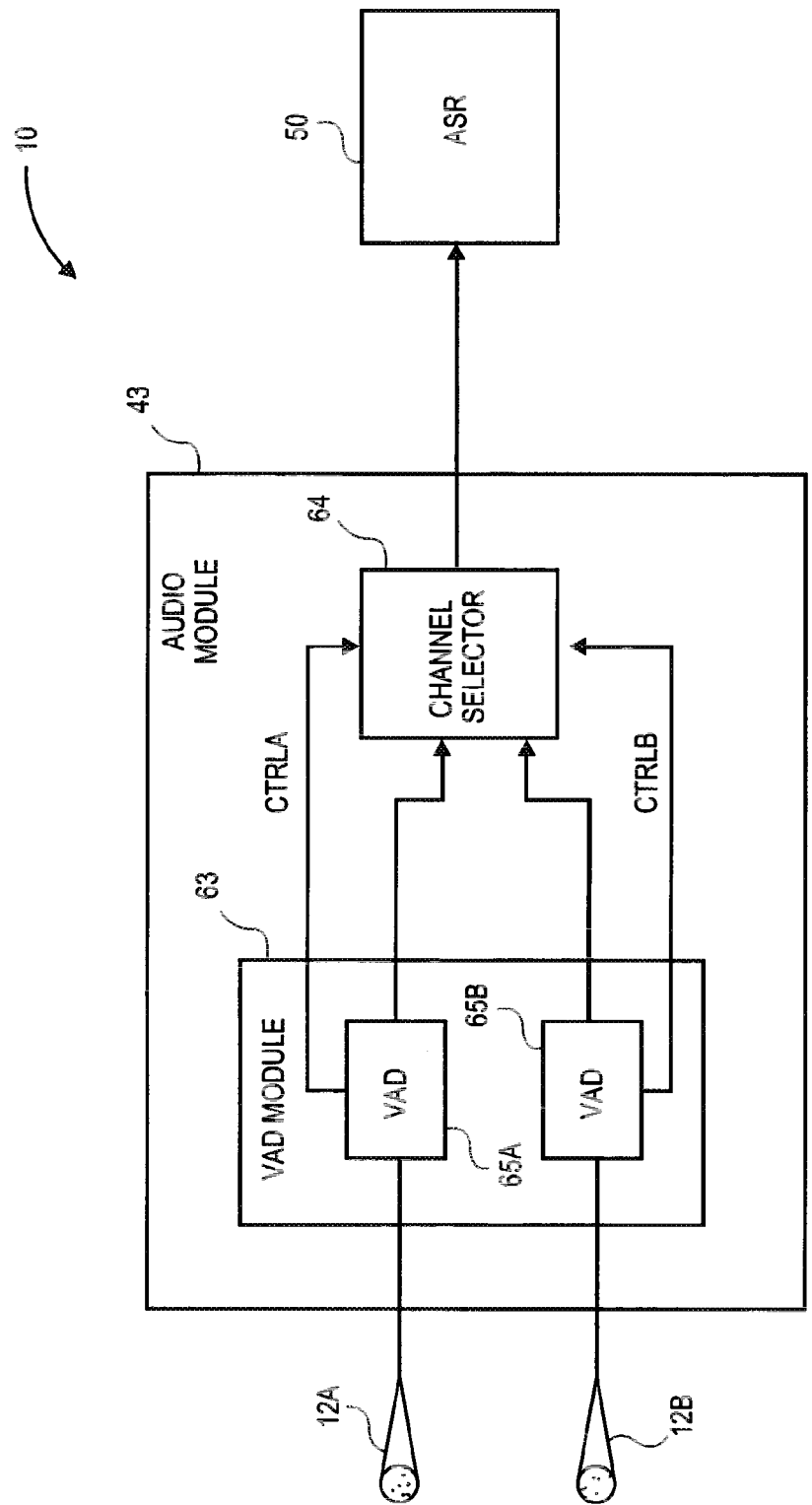

MULTIPLE-USER VOICE-BASED CONTROL OF DEVICES IN AN ENDOSCOPIC IMAGING SYSTEM

FIELD OF THE INVENTION

At least one embodiment of the present invention pertains to endoscopic imaging systems, and more particularly, to a method and apparatus for multiple-user voice-based control of devices in an endoscopic imaging system.

BACKGROUND

Endoscopy in the medical fields allows internal features of a patient's body to be viewed without the use of traditional, fully-invasive surgery. Endoscopy is widely used to perform minimally-invasive medical procedures, such as arthroscopy, laparoscopy, gastroscopy, colonoscopy, etc.

A medical endoscopic imaging system includes an endoscope (or simply "scope"), one end of which is inserted into the body of a patient while the other end of the scope is coupled to a video camera. The scope may be a rigid scope, such as used in arthroscopy or laparoscopy, or a flexible scope, such as used in gastroscopy or colonoscopy. Images acquired by the camera are typically provided to, and displayed on, a conventional display device, such as a cathode ray tube (CRT) or liquid crystal display (LCD) based monitor, which displays live or recorded video. A high intensity light source is normally coupled to the scope by a fiber optic cable, to transmit light through the scope to into the patent's body. The camera may also be coupled to various supporting devices, such as a printer, an image capture unit, and a video recorder.

Some modern endoscopic medical imaging systems also include a voice control system (VCS) that provides centralized voice-based control of various devices in the operating room, including those which are part of the endoscopic imaging system. Speech from a user (e.g., the physician) can be input to the VCS through a microphone mounted on a headset worn by the user. The VCS includes an automatic speech recognizer (ASR) to recognize and generate control signals in response to the user's speech and provides a hierarchy of commands that can be spoken to control various devices, such as the video camera, an image capture unit, etc. An example of a VCS with these capabilities is the Stryker Integrated Device Network (SIDNE) system from Stryker Endoscopy of San Jose, Calif.

It would be advantageous to enable more than one person in the operating room to control devices in the operating room with speech. For example, in addition to the physician having that ability, it would be advantageous if an operating room nurse or other assistant could control certain functions of certain devices. This would reduce the workload on the physician by allowing the nurse or assistant to control various non-critical device functions, such as minor video adjustments, etc., while the physician remains in control of more critical functions, such as camera zoom, image capture, etc.

Known existing VCSs do not provide such capability, however. One problem associated with providing this capability is the potential for speech of one user to interfere with speech of another user. In particular, the speech of a nurse or other assistant could interfere with the physician's voice control of the system, which could result in complicating the overall procedure and putting the patient at risk.

SUMMARY OF THE INVENTION

One aspect of the present invention is a multi-user voice control system for use in endoscopic imaging system. In certain embodiments, the voice control system includes a first input channel, a second input channel, an automatic speech recognizer (ASR), a control unit, and a selector. The first input channel receives speech of a first user, and the second input channel receives speech of a second user. The ASR recognizes speech received on the first channel and recognizes speech received on the second channel. The control unit enables the voice control system to control a device in the endoscopic imaging system in response to recognized speech. The selector selects the first channel or the second channel by applying a selection priority to the first and second channels.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which:

FIG. 4A is a block diagram showing features of the audio module and automatic speech recognizer (ASR) of the VCS;

DETAILED DESCRIPTION

A method and apparatus for multiple-user voice-based control of devices in an endoscopic imaging system are described. In particular, and as described further below, an endoscopic imaging system according to certain embodiments of the invention includes an endoscope and endoscopic video camera, a VCS, an image capture device, and various other supporting devices. The VCS is responsive to speech from one or more users to control functions of the various devices in the endoscopic imaging system. The VCS includes an ASR and two or more audio input channels which can receive speech concurrently from two or more users (e.g., a physician and an assistant), a control unit, and a selector. The ASR is capable of recognizing speech received on any of the audio input channel channels. The selector selectively determines which channel's speech content is recognized or used at any particular time, by applying a selection priority to the audio input channels. The VCS thereby allows two or more users to control the system concurrently using speech. One user, speaker A (e.g., the physician), is given a higher priority than the other user, speaker B (e.g., a nurse). If speakers A and B start speaking simultaneously, the system listens to only speaker A. However, if speaker A is silent and speaker B starts speaking, the system listens to speaker B. The VCS employs an algorithm to ensure that this priority-based switching is done with little or no clipping or omission of speech data during the switching.

Figure 1B:
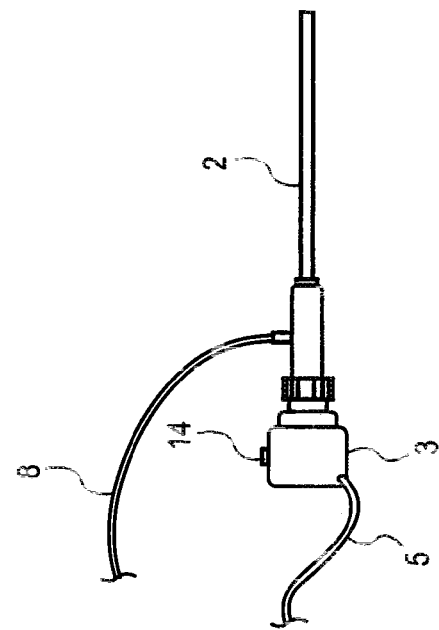
FIGS. 1A and 1B collectively show an example of an endoscopic imaging system.
Figure 1A:
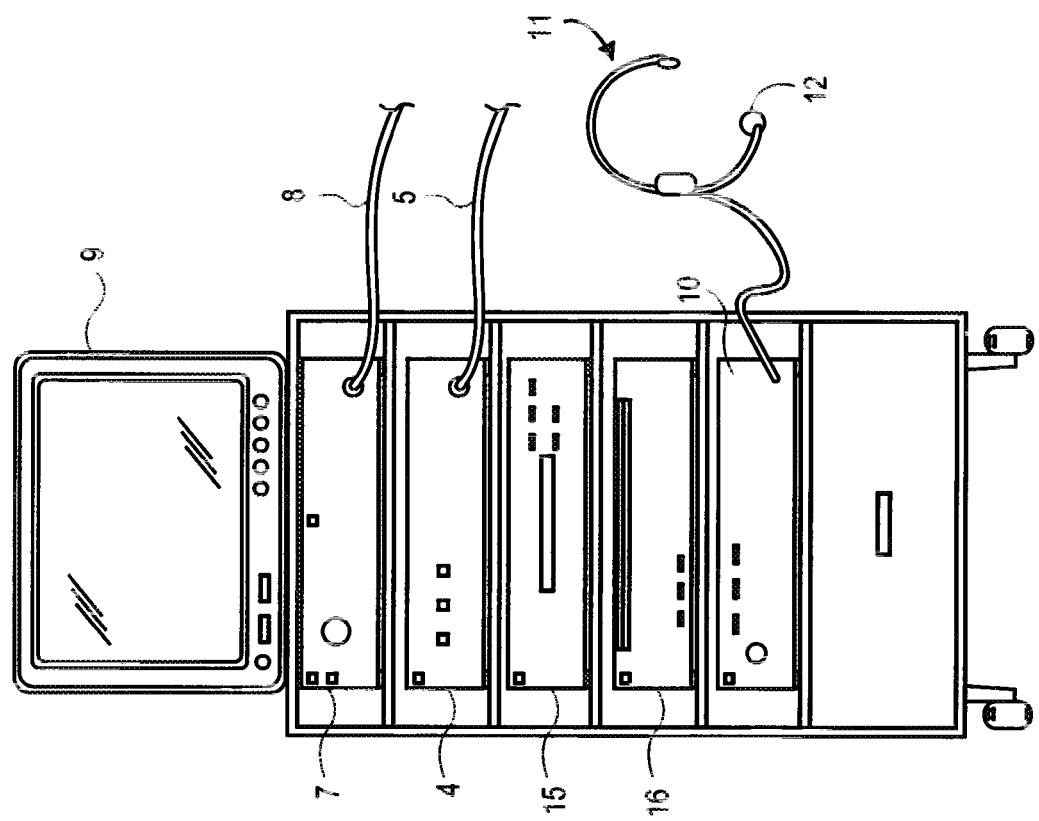

Refer now to FIGS. 1A and 1B, which collectively show an example of an endoscopic imaging system in which a VCS as described above can be used. The illustrated system includes an endoscope ("scope") 2 of the type commonly used for laparoscopy or arthroscopy. The scope 2 is coupled to an endoscopic video camera 3, which includes well-known components for generating color video, based on light received through the scope 2. High intensity light is transmitted into the body of the patient from a light source unit 7 through fiber optic cable 8 and the scope 2. The camera 3 is coupled to camera control unit (CCU) 4 by a flexible electronic transmission line 5. Certain functions of the camera 3 can be controlled from CCU 4. Transmission line 5 conveys video data from the camera 3 to the CCU 4 and also conveys various control signals bi-directionally between the camera 3 and the CCU 4. One or more buttons 14 or other similar manual controls on the camera 3 allows a user to control certain functions of the camera system, such as zoom.

Certain functions of the system can also be controller by voice commands using VCS 10. Speech from a user is input to the VCS 10 through microphone 12 on a headset 11 worn by the user. The VCS 10 includes as ASR (not shown in FIG. 1) to recognize and generate control signals in response to the user's speech.

Also coupled to the CCU 4 are an image capture device (ICD) 15, a printer 16, and perhaps other devices (not shown), as desired. Video acquired by camera 3 is optionally processed by CCU 4 and used to generate images which are displayed on monitor 9. The ICD 15 can record the live video and/or generate static images (i.e. captured video frames) from the live video. Hard copies of captured video frames can be printed by the printer 16.

Figure 2:
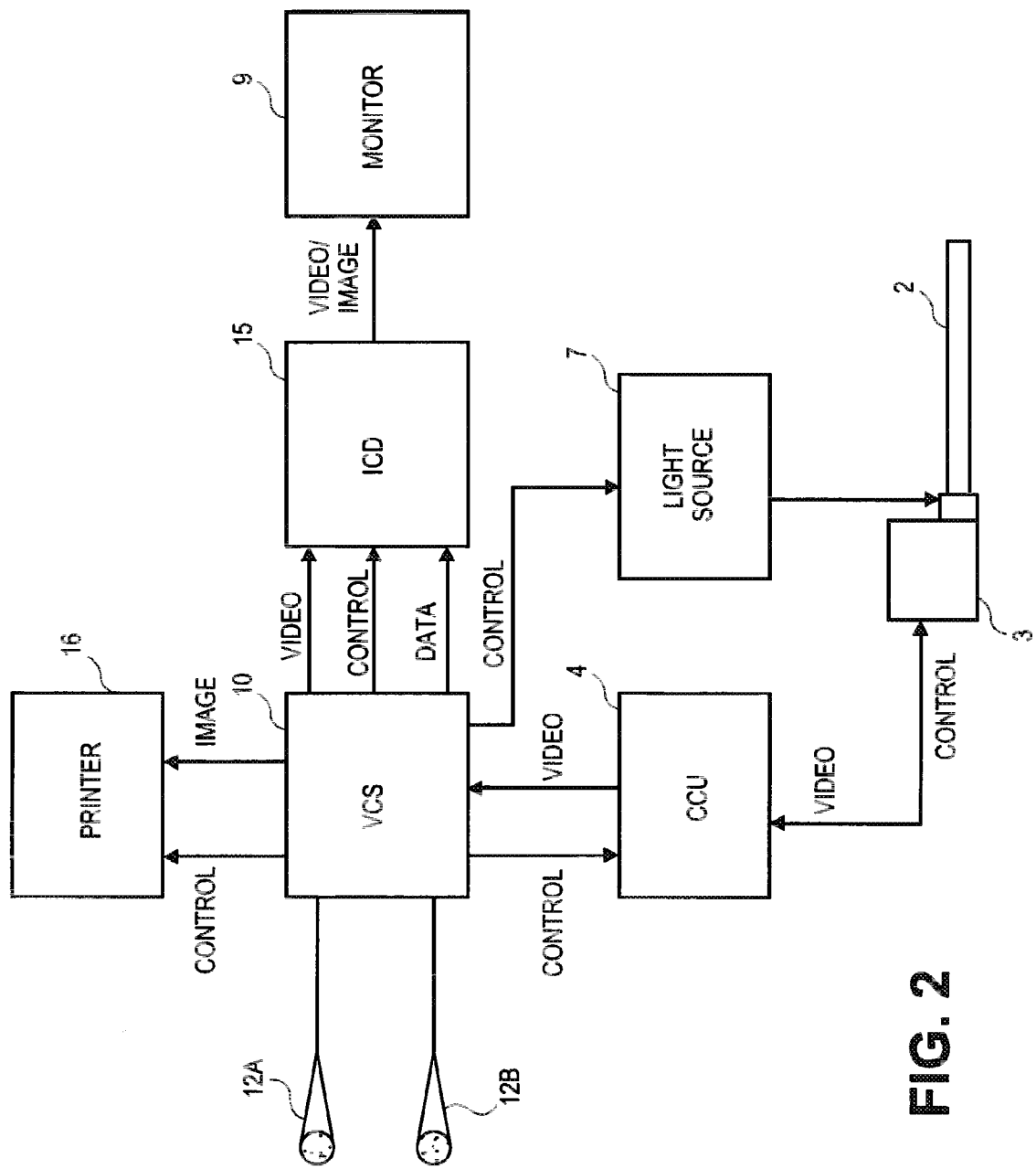
FIG. 2 is a functional block diagram of the endoscopic imaging system of FIG. 1.

FIG. 2 is a block diagram of the endoscopic camera system of FIG. 1, according to certain embodiments. The CCU 4 provides certain basic video processing functions and enables control of certain camera functions, such as control of white balance control, contrast, zoom, etc. Details of the architecture, capabilities and operation of the CCU 4 are not germane to the present invention and therefore need not be described herein.

The VCS 10 provides centralized voice-based control of various devices in the operating room, including any or all of: the CCU 4, the ICD 15, the light source unit 7, the monitor 9, and the printer 16. For each device to be controlled in the operating room, the VCS 10 provides a hierarchy of commands that can be spoken by a user to control that device. By simply speaking the name of a device into the microphone 12, the user can access the menu of commands for that device. The VCS 10 provides separate control outputs CTRL to each of the voice-controllable devices. In addition, the VCS 10 provides separate video and data outputs to at least the ICD 15.

The ICD 15 is a multi-function digital image device. The ICD 15 receives video generated by the endoscopic camera 3 (either directly or through one or more other devices) and provides video output to the external monitor 9 and/or its own built-in display device. The ICD 15 provides the ability to capture live video, i.e., to convert standard analog video into digital format (if necessary), to record the digital video, and to capture video frames as still images. In certain embodiments, the ICD 15 also provides various other capabilities, including the ability to stream live or recorded video over a computer network. An example of a device suitable for use as the ICD 15 is one of the Stryker Digital Capture (SDC) devices from Stryker Endoscopy, such as the Stryker SDC Pro, SDC Pro 2, or SDC HD.

The system may provide the ability to annotate live video based on speech, by cooperation of the VCS 10 with the ICD 15. Live video generated by the camera 3 is routed through the CCU 4 to the VCS 10 and then to the ICD 15. Routing the video through the VCS 10 facilitates synchronization of spoken annotations with the live video stream. Alternatively, the functions of the VCS 10 and the ICD 15 and/or other devices may be provided in a single integrated unit. In addition, the video could alternatively be routed directly from the CCU 4 to the ICD 15.

Figure 3:
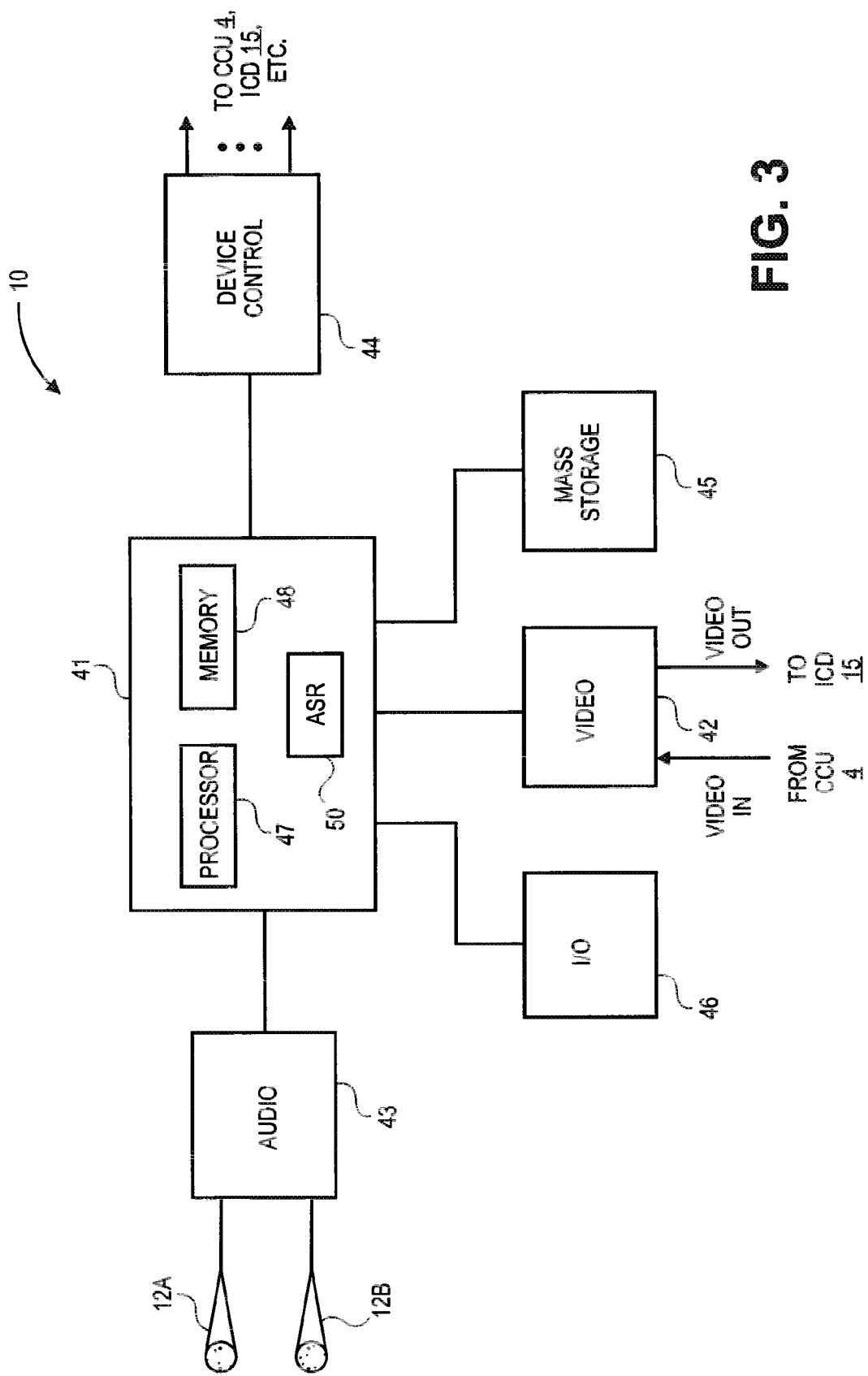
FIG. 3 is a block diagram of the voice-responsive control system (VCS)

FIG. 3 is a block diagram showing the VCS 10 in greater detail. As illustrated, the VCS 10 includes a motherboard 41 coupled to a video board 42, an audio module 43, a device control interface 44, a mass storage device 45, and various I/O controls and/or indicators 46. The motherboard 41 includes one or more processors 47 or other similar control devices as well as one or more memory devices 48. The processor 47 controls the overall operation of the VCS 10 and can include hardwired circuitry, programmable circuitry that executes software, or a combination thereof. The processor 47 may, for example, execute software stored in the memory 48. The processor 47 may include, for example, one or more general- or special-purpose programmable microprocessors and/or microcontrollers, application specific integrated circuits (ASICs), programmable logic devices (PLDs), programmable gate arrays (PGAs), or the like. Memory 48 may include any combination of one or more random access memories (RAMs), read-only memories (ROMs) (which may be programmable), flash memory, and/or other similar storage devices.

In the illustrated embodiment, the motherboard 41 also includes an annotation module (not shown) to allow voice-based annotation of video. The annotation module can be hardwired circuitry, programmable circuitry that executes software, or a combination thereof. The annotation module can be implemented in the processor 47 or as a separate unit. The annotation module can alternatively be located off the motherboard 41, such as in the device control interface 44 or the audio module 43, or it can be distributed between multiple boards/devices within the VCS 10.

The VCS 10 also includes an ASR 50, which may be implemented on the motherboard, as shown, or on the audio board, or distributed between these components. Although shown as a separate unit, the ASR engine 50 could be implemented in the form of the processor 47 executing appropriate software.

The video board 42 can be a simple video input/output (I/O) interface, which includes an input to receive live video from the CCU 4 and an output to provide the received live video to the ICD 15. The audio module 43, which may be implemented in the form of circuitry on a conventional circuit board, has two or more audio inputs to receive speech of two or more users through two or more microphones 12A and 12B, respectively. The microphones 12A and 12B may be mounted on headsets (not shown). To simplify description, it is henceforth assumed herein that there are only two audio channels to support two concurrent users, although more than two concurrent users could easily be supported using essentially the same techniques described herein. The audio module 43 also includes memory and appropriate audio processing circuitry such as is well-known in the art, which may include one or more audio DSPs, PLDs, PGAs, ASICs, etc.

The device control board 44 provides a communication interface between the VCS 10 and other voice-controllable devices to allow the VCS 10 to control those devices. The device control board 44 may include various different types of control/communication interfaces, such as a serial interface (e.g., RS-232, FireWire, or USB), Bluetooth, infrared (IR), etc. The mass storage device 45 may be any type of nonvolatile storage device capable of storing a relatively large volume of data and/or instructions, such as a magnetic or optical disk drive. The details of how devices are controlled by the VCS 10 and the protocols used are not germane to the present invention and need not be described herein.

FIG. 4A shows a portion of the VCS 10 in greater detail, according to an embodiment of the invention. As shown, the VCS 10 includes audio module 43 and the ASR 50. As described further below, the audio module 43 includes features which allow two users, speaker A and speaker B, to control the system concurrently using speech. In certain embodiments of the invention, speaker A using microphone 12A (e.g., the physician) is given a higher priority than speaker B using microphone 12B (e.g., a nurse). According to certain embodiments of the invention, if speakers A and B start speaking simultaneously, the system listens only to speaker A; if speaker A is silent and speaker B starts speaking, the system listens to speaker B; if speaker B starts speaking while speaker A is already speaking, then the system listens only to speaker A; and if speaker A starts speaking while speaker B is already speaking, then the system listens only to speaker A because speaker A has higher priority.

As shown, the audio module 43 includes a voice activity detector (VAD) module 63 and a channel selector 64, connected in series (functionally) between the microphones 12A and 12B and the ASR 50. In the illustrated embodiment, the VAD module 63 includes two separate VADs 65A and 65B for microphones 12A and 12B, respectively, although the functions of VADs 65A and 65B can be combined into a single physical unit.

Figure 5:
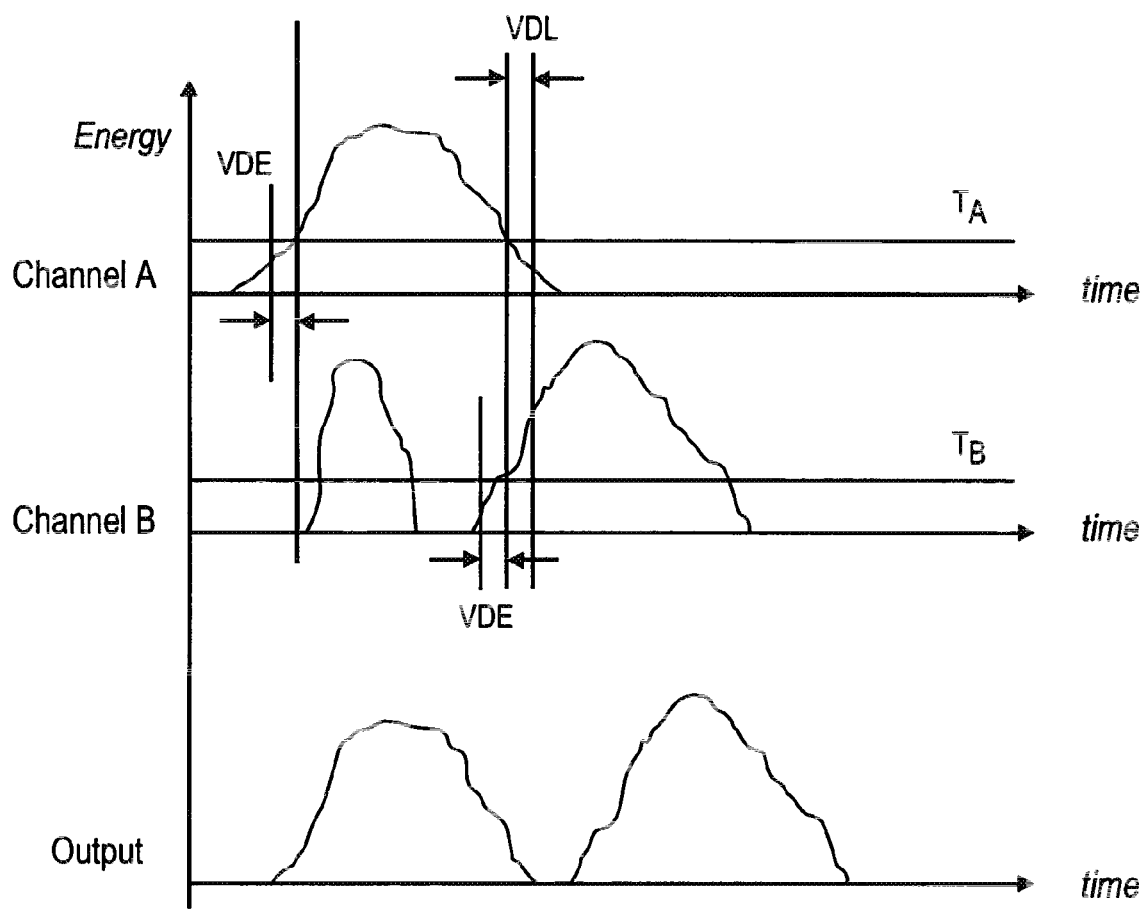
FIG. 5 is a signal diagram showing the relationships between the audio signals on channel A and channel B and the output of the channel selector, for one scenario.

Each VAD 65A or 65B is responsible for determining when voice is present (as opposed to only silence or background noise) in the input signal from its respective microphone 12A or 12B. Devices which perform such a function are well-known. This can be done by comparing the energy of the signal from the microphone to a threshold value. As illustrated in FIG. 5, VADs 65A and 65B use thresholds $T_A$ and $T_B$, respectively, to determine whether voice is present in the input signals from microphones 12A and 12B, respectively. Thresholds $T_A$ and $T_B$ can be set equal, although that is not necessarily so. The thresholds $T_A$ and $T_B$ can be predetermined values, i.e., values that are set in the VCS 10 at the manufacturer and/or during a system setup phase. These values may be default values or user-specified values. Further, the thresholds $T_A$ and $T_B$ can be adjustable during operation of the VCS 10, either by a user or automatically (e.g., adaptively).

Each VAD 65A or 65B passes the audio signal which it monitors through to the channel selector 64. Also, each VAD 65A or 65B supplies to the channel selector 64 a control signal which indicates whether the audio signal monitored by that VAD contains voice. In the illustrated embodiment, the channel selector 64 selects the signal from microphone 12A or the signal from microphone 12B (but not both at the same time) to pass through to the ASR 50, for recognition, based on the states of control signals CTRLA and CTRLB from VADs 65A and 65B, respectively. It will be recognized that the channel selector 64 is essentially a multiplexor.

In certain embodiments, the channel selector 64 makes the selection by applying a simple logic function to the control signals CTRLA and CTRLB. For example, in certain embodiments, channel A (microphone 12A) is designated as the primary channel, e.g., for use by the physician, while channel B (microphone 12B) is designated as the secondary channel. Accordingly, channel A is assigned a higher priority than channel B. In certain embodiments, therefore, the channel selector 64 selects channel A to pass through to the ASR 50 whenever voice is present on channel A (i.e., the energy of the signal on channel A exceeds threshold $T_A$, as indicated by control signal CTRLA), regardless of whether voice is present on channel B; on the other hand, the channel sector 64 selects channel B to pass through to the ASR 50 only if voice is not present on channel A and voice is present on channel B (i.e., the energy of the signal on channel A is below threshold $T_A$, as indicated by control signal CTRLA, and the energy of the signal on channel B exceeds threshold $T_B$, as indicated by control signal CTRLB). In certain embodiments of the invention, the prioritization of channels A and B can be implemented at least partly by appropriately setting the thresholds $T_A$ and $T_B$ to different values. For example, $T_A$ can be set to a lower value than $T_B$, thus making it more likely that speech from speaker A will be detected than speech from speaker B. However, this could cause more noise to be detected on channel A, degrading recognition accuracy, or cause false triggering of the channel selector 64.

Figure 4B:
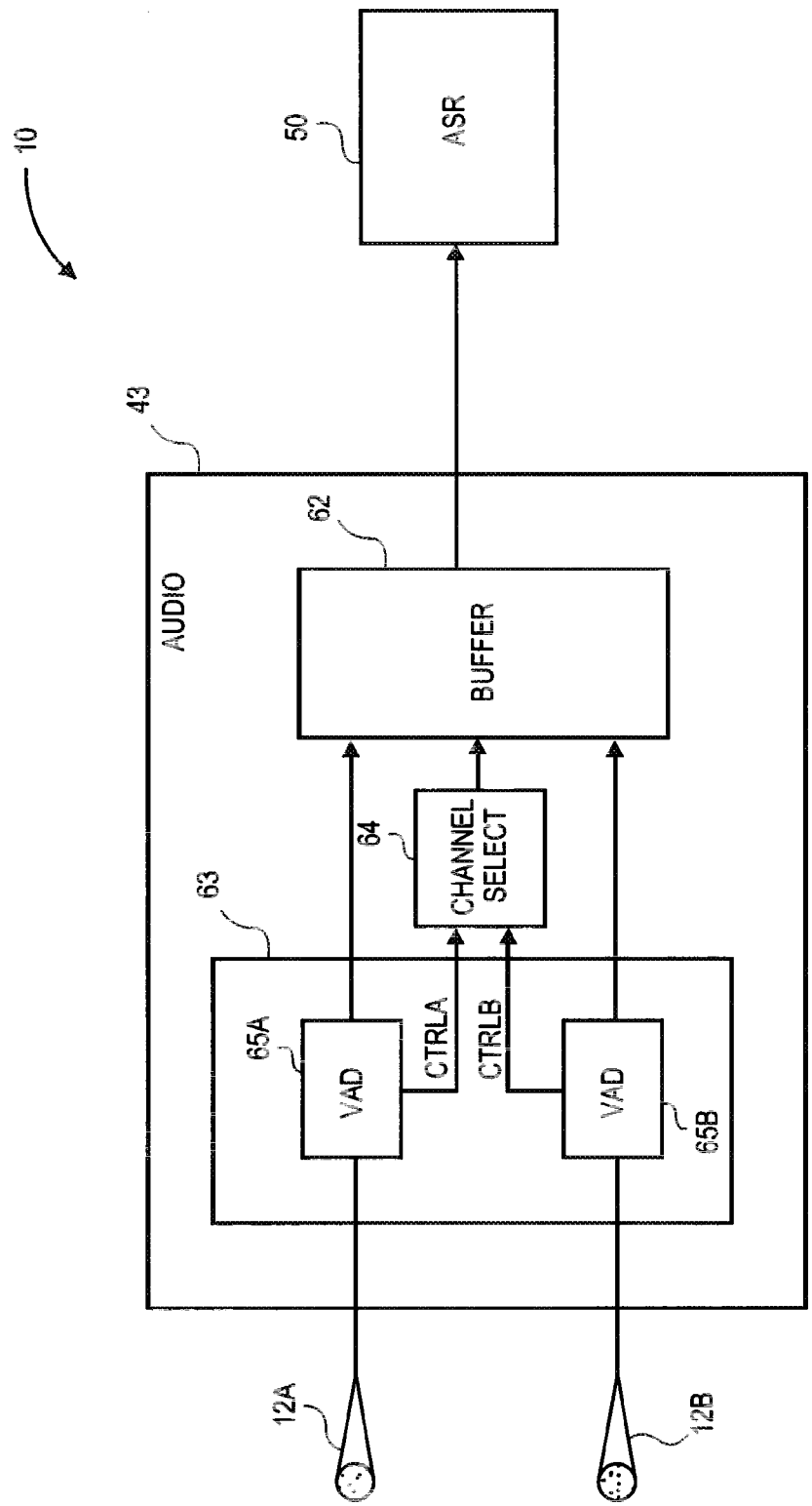
FIG. 4B is a block diagram showing features of the audio module and ASR, for an embodiment which employs buffering of the input audio signals.

In a simple embodiment, the approach described above would cause clipping of any portion of the audio signal which is below the applicable threshold level $T_A$ or $T_B$, degrading the quality of speech recognition. However, the audio module 43 employs an algorithm to ensure that this priority-based switching is done so that little or no clipping or omission of speech data occurs during switching. To avoid such effects, the audio module 43 continuously buffers (delays) a portion of the audio signal from each microphone 12A and 12B, in a first-in first-out (FIFO) manner. The buffer's contents thereby form a temporally sliding window of a segment of each audio signal. Such an embodiment is illustrated in FIG. 4B, in which the buffer 62 receives and buffers the audio signals from both channel A and channel B. The output of the channel selector 64 in this embodiment is just a control input that indicates to the buffer 62 whether to output the buffered channel A signal or the buffered channel B signal to the ASR 50 at any point in time.

The duration of the delay (i.e., the amount of signal which is buffered) is predetermined and is chosen to be short enough so as to have no noticeable impact on the response time of the VCS 10, for example 10-15 msec. The length of the delay is also chosen with respect to the applicable threshold level and typical human speech; specifically, the length of the delay is chosen to be a significant fraction of the typical length of time it takes for the energy of the audio signal to go from baseline to threshold at the beginning of an utterance or to fall from threshold to baseline at the end of an utterance.

Referring to FIG. 5, when selection of a particular audio channel A or B is triggered by the signal exceeding the applicable threshold $T_A$ or $T_B$, most of the leading below-threshold portion of the signal will still be present in the buffer and therefore will be passed to the ASR 50 in the proper sequence when the channel selector 64 selects that channel. Likewise, when the signal subsequently falls below the threshold at the end of the utterance, most of the trailing below-threshold portion of the signal will still be present in the buffer and therefore will be passed to the ASR 50 in the proper sequence for recognition. The buffered leading below-threshold portion of the signal is referred to herein as the early delay, or VDE, as shown in FIG. 5. The buffered trailing below-threshold portion of the signal is referred to herein as the late delay, or VDL, as shown in FIG. 5.

FIG. 5 shows an example of the signals for a situation in which speaker A starts speaking first, and then speaker B starts speaking before speaker A has finished speaking. The signal labeled Output represents the output of the channel selector 64, or the input to the ASR 50. The audio module 43 passes a signal through to the ASR 50 only when the energy from a microphone 12A or 12B exceeds a specified threshold level, $T_A$ or $T_B$. In the embodiment of FIG. 4A, this would cause clipping of the trailing below-threshold segment of the signal from microphone 12A and the leading below-threshold segment of the signal from microphone 12B, degrading the quality of speech recognition. However, the above-mentioned buffering avoids that effect. This functionality and other functions of the audio module 43 can be implemented using an audio DSP, to ensure fast operation and no noticeable difference to the user.

As described above, the priority-based channel selection functionality is implemented in the audio module 43 of the VCS 10. In other embodiments, however, that functionality may be implemented in a different functional unit, such as in the ASR 50, or it may be distributed between two or more functional units.

Note that various well-known types of signal conditioning may be applied at various stages in the above-described process and system, for example, in the audio module 43. Such signal conditioning techniques, if used, are not germane to the invention and need not be described herein.

Figure 6:
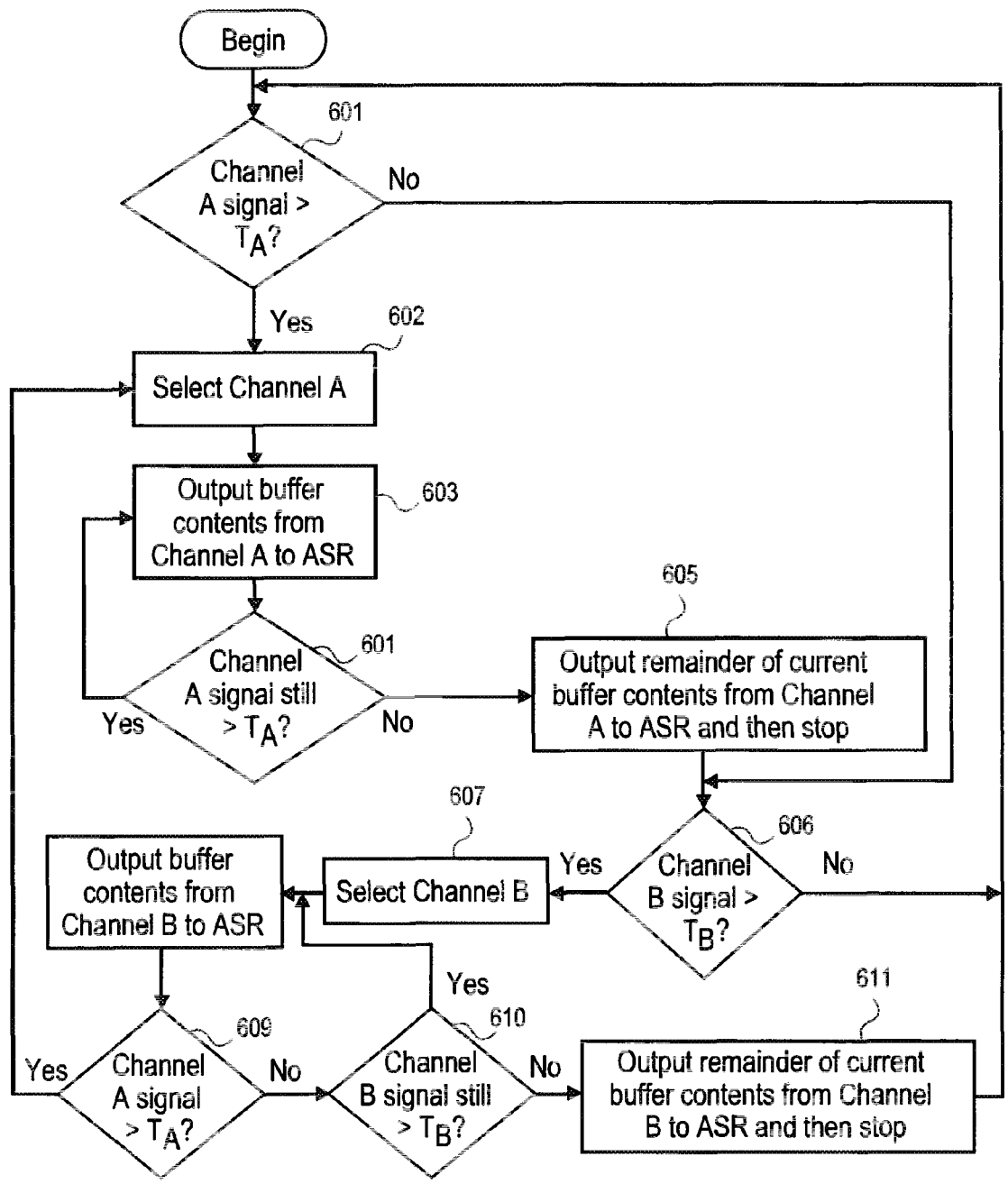
FIG. 6 is a flow diagram of a process that may be performed by the audio module in the VCS.

FIG. 6 shows an example of a process that may be performed by the audio module 43 to selectively provide an audio signal to the ASR 50, in an embodiment according to FIG. 4B. Initially, if the energy level of the signal on channel A is greater than threshold $T_A$ at block 601, then the channel selector 64 selects channel A at block 602 and causes the buffer contents for channel A to be provided to the ASR 50 at block 603. If, however, the energy level of the signal on channel A is not greater than threshold $T_A$ at block 601, then the process skips to block 606, described below.

After block 603, if the energy level of the signal on channel A is still greater than threshold $T_A$ at block 604, then the process loops back to block 603; otherwise, the process continues from block 605. In block 605, only the current contents of the buffer for channel A are output to the ASR 50, after which the outputting from the buffer stops.

After block 605 or block 601, provided that the energy level of the signal on channel A after block 601 is less than the threshold $T_A$, if the energy level of the signal on channel B is greater than threshold $T_B$ at block 606, then the channel sector 64 selects channel B at block 607 and causes the buffer contents for channel B to be provided to the ASR 50 at block 608. If the energy level of the signal on channel B is not greater than threshold $T_B$ at block 606, then the process loops back to block 601, as described above.

After block 608, the system again tests whether the energy level of the signal on channel A is greater than threshold $T_A$ at block 609; this test effectively gives priority to channel A over channel B. If the energy level of the signal on channel A is greater than threshold $T_A$ at block 609, the process loops back to block 602, where channel A is again selected. If the energy level of the signal on channel A is not greater than threshold $T_A$ at block 609, then the system tests whether the energy level of the signal on channel B is still greater than threshold $T_B$ at block 610; if so, then at block 611, only the current contents of the buffer for channel B are output to the ASR 50, after which the outputting from the buffer stops, and the process then loops back to block 601.

Thus, a method and apparatus for multiple-user voice-based control of devices in an endoscopic imaging system have been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A multi-user voice control system for use in an endoscopic imaging system, the multi-user voice control system comprising:
    a first input channel to receive speech of a first user of the endoscopic imaging system;
    a second input channel to receive speech of a second user of the endoscopic imaging system, wherein the first and second input channels are formed in a single device;
    a selection unit to select the first input channel or the second input channel by applying a selection priority to the first and second input channels, wherein the selection unit comprises a voice activity detector (VAD) module to determine a first signal received on the first input channel when the first user starts speaking exceeds a first threshold and to determine whether a second signal received on the second input channel exceeds a second threshold, wherein the first threshold is less than the second threshold;
    an automatic speech recognizer (ASR) to recognize speech received on a channel selected by the channel selector; and
    a control unit to enable the multi-user voice control system to control a device in the endoscopic imaging system in response to speech recognized by the ASR.

2. A multi-user voice control system as recited in claim 1, wherein the selection unit is to selectively determine whether recognized speech associated with the first input channel or recognized speech associated with the second input channel is used to control the device, by applying the selection priority to the first and second input channels.

3. A multi-user voice control system as recited in claim 1, wherein the selection unit is to pass the first signal for recognition by the ASR and to not pass the second signal for recognition by the ASR, when the first signal exceeds the first threshold.

4. A multi-user voice control system as recited in claim 3, wherein the selection unit further is to pass the second signal for recognition by the ASR only when the second signal exceeds the second threshold while the first signal is below the first threshold.

5. A multi-user voice control system as recited in claim 1, further comprising a device control interface through which to communicate with the device.

6. A multi-user voice control system as recited in claim 1, the endoscopic imaging system including a plurality of voice-controllable devices, the multi-user voice control system further comprising:
    means for allowing speech received on the first input channel to control any of the plurality of voice-controllable devices; and
    means for allowing speech received on the second input channel to control only a subset of the plurality of voice-controllable devices.

7. A multi-user voice control system as recited in claim 1, wherein the selection unit overrides the selection priority in response to a predetermined utterance on the second input channel and selects the second input channel.

8. A multi-user voice control system as recited in claim 1, further comprising:
   means for buffering a segment of a first signal received on the first input channel, which is below a first threshold; and
   means for providing the buffered segment of the first signal to the ASR for recognition.

9. A multi-user voice control system as recited in claim 8, wherein said buffering comprises buffering a sliding segment of the first signal.

10. A multi-user voice control system as recited in claim 8, further comprising:
    means for buffering a segment of a second signal received on the second input channel, which is below a second threshold; and
    means for providing the buffered segment of the second signal to the ASR for recognition.

11. A multi-user apparatus for use in an endoscopic imaging system, the apparatus comprising:
    a first input channel to receive a first signal representing speech of a first user of the endoscopic imaging system;
    a second input channel to receive a second signal representing speech of a second user of the endoscopic imaging system, wherein the first and second input channels are formed in a single device;
    means for selecting the first signal and ignoring the second signal when the first signal exceeds a first threshold, and for selecting the second signal when the second signal exceeds a second threshold and the first signal is below the first threshold, wherein the means for selecting comprises a voice activity detection means to determine whether a first signal received on the first input channel when the first user starts speaking exceeds a first threshold and to determine whether a second signal received on the second input channel exceeds a second threshold, wherein the first threshold is less than the second threshold;
    an automatic speech recognizer (ASR) to recognize speech of the first or second user from a signal selected by the selecting means; and
    means for controlling a device in the endoscopic imaging system external to the apparatus in response to speech of the first user or the second user recognized by the ASR.

12. A multi-user apparatus as recited in claim 11, wherein the endoscopic imaging system includes a plurality of voice-controllable devices; the voice control system further comprising:
    means for allowing speech received on the first input channel to control any of the plurality of voice-controllable devices; and
    means for allowing speech received on the second input channel to control only a subset of the plurality of voice-controllable devices.

13. A multi-user apparatus as recited in claim 11, wherein the selecting means selects the second signal in response to a predetermined utterance on the second input channel regardless of whether the first signal exceeds the first threshold.

14. A multi-user apparatus as recited in claim 11, further comprising:
    means for buffering a segment of the first signal which is below the first threshold; and
    means for providing the buffered segment of the first signal to the ASR for recognition.

15. A multi-user apparatus as recited in claim 14, wherein said buffering comprises buffering a sliding segment of the first signal.

16. A multi-user apparatus as recited in claim 15, further comprising:
    means for buffering a segment of the second signal which is below the second threshold; and
    means for providing the buffered segment of the second signal to the ASR for recognition.

17. A method of controlling a device in an endoscopic imaging system based on speech, the method comprising:
    receiving speech of a first user on a first channel and speech of a second user on a second channel, wherein the first and second users are users of the endoscopic imaging system, and the first and second channels are formed in a single device;
    determining whether speech associated with the first channel or speech associated with the second channel will be used to control the device in the endoscopic imaging system, by applying a prioritization to the first and second channels wherein said determining comprises
        determining whether a first signal received on the first channel when the first user starts speaking exceeds a first threshold, and
        determining whether a second signal received on the second channel exceeds a second threshold, wherein the first threshold is less than the second threshold;
    automatically recognizing speech of the first or second user according to a result of said determining; and
    using the automatically recognized speech to control the device.

18. A method as recited in claim 17, wherein said determining comprises passing the first signal for automatic speech recognition and not passing the second signal for automatic speech recognition, if the first signal exceeds the first threshold.

19. A method as recited in claim 18, wherein said determining comprises passing the second signal for automatic speech recognition only if the second signal exceeds the second threshold and the first signal is below the first threshold.

20. A method as recited in claim 18, further comprising:
    buffering a segment of the first signal which is below the first threshold; and
    providing the buffered segment of the first signal to an automatic speech recognizer for recognition.

21. A method as recited in claim 20, wherein said buffering comprises buffering a sliding segment of the first signal.

22. A method as recited in claim 20, further comprising:
    buffering a segment of the second signal which is below the second threshold; and
    providing the buffered segment of the second signal to the automatic speech recognizer for recognition.

23. A method as recited in claim 18, further comprising:
    buffering a sliding segment of the first signal, including a segment of the first signal which is below the first threshold;
    providing the buffered segment of the first signal, including the segment of the first signal which is below the first threshold, to an automatic speech recognizer for recognition;
    buffering a sliding segment of the second signal, including a segment of the second signal which is below the second threshold; and providing the buffered segment of the second signal, including the segment of the second signal which is below the second threshold, to the automatic speech recognizer for recognition.

24. A method as recited in claim 17, wherein the endoscopic imaging system includes a plurality of voice-controllable devices; the method further comprising:
allowing speech received on the first channel to control each of the plurality of voice-controllable devices; and
allowing speech received on the second channel to control only a subset of the plurality of voice-controllable devices.

25. A method as recited in claim 17, wherein the prioritization is such that the first channel has a higher priority than the second channel; and the determining further comprises overriding the prioritization in response to a predetermined utterance on the second channel, and determining that speech associated with the second channel will be used to control the device in the endoscopic imaging system.

26. A method comprising:
receiving a first signal representing speech of a first user on a first channel and a second signal representing speech of a second user on a second channel, wherein the first and second users are users of an endoscopic imaging system, and the first and second channels are formed in a single device;
if the first signal exceeds a first threshold when the first user starts speaking, then enabling automatic speech recognition with respect to the first signal while preventing automatic speech recognition with respect to the second signal;
if the second signal exceeds a second threshold while the first signal is below the first threshold, then enabling automatic speech recognition with respect to the second signal, wherein the first threshold is less than the second threshold; and
controlling a device in the endoscopic imaging system in response to the recognized speech.

27. A method as recited in claim 26, further comprising:
buffering a segment of the first signal which is below the first threshold; and
providing the buffered segment of the first signal to an automatic speech recognizer for recognition.

28. A method as recited in claim 27, wherein said buffering comprises buffering a sliding segment of the first signal.

29. A method as recited in claim 27, further comprising:
buffering a segment of the second signal which is below the second threshold; and
providing the buffered segment of the second signal to the automatic speech recognizer for recognition.

30. A method as recited in claim 26, further comprising:
buffering a sliding segment of the first signal, including a segment of the first signal which is below the first threshold;
providing the buffered segment of the first signal, including the segment of the first signal which is below the first threshold, to an automatic speech recognizer for recognition;
buffering a sliding segment of the second signal, including a segment of the second signal which is below the second threshold; and
providing the buffered segment of the second signal, including the segment of the second signal which is below the second threshold, to the automatic speech recognizer for recognition.

31. A method as recited in claim 26, wherein the method is performed in a voice control system within the endoscopic imaging system that includes a plurality of voice-controllable devices, the method further comprising:
allowing speech received on the first channel to control any of the plurality of voice-controllable devices; and
allowing speech received on the second channel to control only a subset of the plurality of voice-controllable devices.

32. A method of operating a voice control system (VCS) for controlling a voice-controllable device in an endoscopic imaging system, the method comprising:
receiving at the VCS a first signal for conveying speech of a first user on a first channel, wherein the first user is a user of the endoscopic imaging system;
receiving at the VCS a second signal for conveying speech of a second user on a second channel, wherein the second user is a user of the endoscopic imaging system, and the first and second channels are formed in a single device;
buffering a sliding segment of the first signal and a sliding segment of the second signal;
detecting when the first signal exceeds a first threshold and detecting when the second signal exceeds a second threshold;
in response to the first signal exceeding the first threshold when the first user starts speaking, enabling automatic speech recognition to be performed with respect to the first signal, including a leading segment and a trailing segment of the first signal which are below the first threshold, in the VCS, while preventing automatic recognition from being performed with respect to the second signal;
in response to the second signal exceeding the second threshold while the first signal is below the first threshold, enabling automatic speech recognition to be performed with respect to the second signal, including a leading segment and a trailing segment of the second signal which are below the second threshold, in the VCS, wherein the first threshold is less than the second threshold; and
using recognized speech associated with the first or second signal to control the voice-controllable device.

33. A method as recited in claim 32, wherein the endoscopic imaging system includes a plurality of voice-controllable devices; the method further comprising:
allowing speech received on the first channel to control any of the plurality of voice-controllable devices; and
allowing speech received on the second channel to control only a subset of the plurality of voice-controllable devices.

34. A method as recited in claim 32, further comprising in response to a predetermined utterance on the second channel, enabling automatic speech recognition to be performed with respect to the second signal, including a leading segment and a trailing segment of the second signal which are below the second threshold, in the VCS, regardless of whether the first signal exceeds the first threshold.

* * * * *